United States Patent [19]

Palva

[11] Patent Number: 5,010,015

[45] Date of Patent: Apr. 23, 1991

[54] RECOMBINANT DNA-MOLECULES AND METHOD FOR PROTEIN PRODUCTION

[75] Inventor: Ilkka Palva, Helsinki, Finland

[73] Assignees: Genesit Oy; Oy Alko AB, both of Helsinki, Finland

[21] Appl. No.: 129,357

[22] Filed: Nov. 30, 1987

Related U.S. Application Data

[63] Continuation of Ser. No. 939,244, Dec. 5, 1986, abandoned, which is a continuation of Ser. No. 336,405, Dec. 31, 1981, abandoned.

[30] Foreign Application Priority Data

Dec. 31, 1980 [FR] France ................................ 804081

[51] Int. Cl.$^5$ .................... C12P 21/00; C12N 15/00; C12N 1/20; C12N 9/86

[52] U.S. Cl. ................... 435/320; 435/69.1; 435/69.51; 435/69.7; 435/69.8; 435/71.2; 435/172.3; 435/231; 435/252.31; 435/320; 536/27; 935/48; 935/74

[58] Field of Search ................... 435/68, 70, 71, 91, 435/172.1, 172.3, 183, 202, 243, 253, 320, 252.3, 252.31-252.35, 69.1, 69.51, 69.7, 69.8, 71.2, 231; 536/27; 935/9-15, 29, 33, 38, 47, 48, 74

[56] References Cited

U.S. PATENT DOCUMENTS 4,338,397  7/1982  Gilbert et al. .......................... 435/68

FOREIGN PATENT DOCUMENTS

| | | | |
|---|---|---|---|
| 0001929 | 5/1979 | European Pat. Off. . | |
| 0003062 | 7/1979 | European Pat. Off. . | |
| 0006694 | 1/1980 | European Pat. Off. | 435/172.3 |
| 0034470 | 8/1981 | European Pat. Off. | 435/172.3 |
| 0036259 | 9/1981 | European Pat. Off. | 435/172.3 |
| 0021468 | 4/1983 | European Pat. Off. | 435/172.3 |
| 1521032 | 8/1978 | United Kingdom | 435/172.3 |
| 2031905 | 4/1980 | United Kingdom | 435/172.3 |
| 1588572 | 4/1981 | United Kingdom | 435/172.3 |
| 2071671 | 9/1981 | United Kingdom | 435/172.3 |

OTHER PUBLICATIONS

Palva et al., "Nucleotide Sequence of the Promoter and NH$_2$-Terminal Signal Peptide Region of the Alpha-Amylase Gene from Bacillus Amyloliquefaciens", Gene 15:43 (1981).

Yoneda et al.: Biochem. Biophys. Res. Comm. 91, 1556 (1979).

Gryczan et al.: Molec. Gen. Genet. 177, 459 (1980).

Keggins et al.: Proc. Natl. Acad. Sci. U.S.A. 75, 1423 91978).

Nagata et al.: Nature 287, 401 (1980).

Lovett and Keggins, *Meth. Enzymol.* 68: 342-357 (1979).

Priest, *Bacteriol. Rev.* 41(3): 711-753 (1977).

Palva et al., *Gene* 15: 43-51 (1981).

Palva, *Gene* 19: 81-87 (1982).

Palva et al., Proc. Natl. Acad. Sci., U.S.A., 79: 5582-5586 (1982).

Palva et al., Gene 22: 229-235 (1983).

Blubel et al.; J. Cell Biol. 67,835 (1975).

(List continued on next page.)

*Primary Examiner*—James Martinell
*Attorney, Agent, or Firm*—Sterne, Kessler, Goldstein & Fox

[57] ABSTRACT

The invention relates to recombinant DNA molecules and to methods for producing proteins by means of said molecules. Particularly, the present invention relates to recombinant DNA molecules which are synthetized in Bacillus strain bacteria and are characterized by DNA which codes for exoenzymes excreted by a bacterium of the Bacillus strain and which are present in tens of copies in Bacillus strain bacteria, as well as to recombinant DNA molecules which are modified from the above recombinant DNA molecules and are characterized by DNA containing the regulation and excretion signals of the α-amylase gene of *B. amyloliquefaciens*, to which signals a gene of any protein can be joined. These recombinant DNA molecules can be used, for example, to improve the production of α-amylase in Bacillus strain bacteria, and their modifications to produce any protein in Bacillus strain bacteria.

6 Claims, 4 Drawing Sheets

OTHER PUBLICATIONS

Waksman et al.: Biochem. Biophys. Acta 604, 249 (1980).
Priest: Bacteriol. Rev. 41, 711 (1977).
Palva: Gene 19, 81 (1982).
Lai et al.: Proc. Natl. Acad. Sci. U.S.A. 78, 3506 (1981).
Nielsen et al.: Proc. Natl. Acad. Sci. U.S.A. 78, 3511 (1981).
Casadaban: Proc. Natl. Acad. Sci. U.S.A. 72, 809 (1975).
Mantei et al., *Gene*, 10: 1–10 (1980).
Maxam et al., *Proc. Natl. Acad. Sci.*, U.S.A., 74: 560–564 (1977).
Nagata et al., *Nature*, 284: 316–320 (1980).
Streuli et al., *Science*, 209: 1343–1347 (1980).
Nagata et al., *Nature*, 287: 401–408 (1980).
Lawn et al., *Science*, 212: 1159–1162 (1981).
Taniguchi et al., *Gene, 10: 11–15 (1980)*.
Martial et al., *Science*, 205: 602–607 (1979).
Taniguchi et al., *Nature*, 285: 547–549 (1980).
Goeddel et al., *Nature*, 281: 544–548 (1979).
Gross et al., *Nucleic Acid Res.* 9: 2495–2507 (1981).
Roskam et al., *Nucleic Acid Res.*, 7: 305–320 (1979).
DeNoto, et al., *Nucleic Acid Res.*, 9: 3719–3730 (1981).
Page, et al., *Nucleic Acid Res.* 9: 2087–2104 (1981).
Miller et al., *J. Biol. Chem.*, 255: 7521–7524 (1980).
Barta et al., Proc. Natl. Acad. Sci. U.S.A., 78: 4867–4871 (1981).
Seeburg et al., *Nature*, 270: 486–494 (1977).
Itakura et al., *Science, 198: 1056–1063 (1977)*.
Seeberg et al., *Cell*, 12: 157–165 (1977).
Ullrich et al., *Science*, 209: 612–615 (1980).
Shine et al., *Nature*, 270: 494–499 (1977).
Hobart et al., *Science*, 210: 1360–1363 (1980).
Bell et al., *Nature*, 284: 26–32 (1980).
Cordell et al., *Cell*, 18: 533–543 (1979).
Sanger et al., *Proc. Natl. Acad. Sci., U.S.A.*, 74: 5463–5467 (1977).
Maniatis et al., *Cell*, 15: 687–701 (1978).
Sutcliffe, *Proc. Natl. Acad. Sci., U.S.A.*, 75: 3737–3741 (1978).
Efstratiditis et al., *Cell*, 7: 279–233 (1976).
Southern, *Method Enzymol.*, 68: 152–176 (1979).
Khorana, *Science*, 203: 614–625 (1973).
Scheller et al., *Science*, 196: 177–180 (1977).
Blattner et al., *Science*, 196: 161–169 (1977).
Mandel et al., *J. Mol. Biol.*, 53: 159–162 (1970).
Bolivar et al., *Gene*, 2: 75–93 (1977).
Hanahan et al., *Gene*, 10: 63–67 (1980).
Alwine et al., *Method Enzymol.*, 68: 220–242 (1979).
Bolivar et al., *Gene*, 2: 95–113 (1977).
Thomas, *Proc. Natl. Acad. Sci., U.S.A.*, 77: 5201–5205 (1980).
Yoneda et al., *Biochem. Biophys. Res. Comm.*, 91: 1556–1564 (1979).
Broome et al., *Proc. Natl. Acad. Sci. U.S.A.*, 75: 2746–2749 (1978).
Gryczan, et al., *Molec. Gen. Genet.*, 177: 459–467 (1980).

```
         10         20         30         40         50         60
5' AAGCCCCGCA CATACGAAAA GACTGGCTGA AAACATTGAG CCTTTGATGA CTGATGATTT
3' TTCGGGGCGT GTATGCTTTT CTGACCGACT TTTGTAACTC GGAAACTACT GACTACTAAA 70         80         90        100        110        120
   GGCTGAAGAA GTGGATCGAT TGTTTGAGAA AAGAAGAAGA CCATAAAAAT ACCTTGTCTG
   CCGACTTCTT CACCTAGCTA ACAAACTCTT TTCTTCTTCT GGTATTTTTA TGGAACAGAC 130        140        150        160        170        180
   TCATCAGACA GGGTATTTTT TATGCTGTCC AGACTGTCCG CTGTGTAAAA ATAAGGAATA
   AGTAGTCTGT CCCATAAAAA ATACGACAGG TCTGACAGGC GACACATTTT TATTCCTTAT 190        200        210        220        230        240
   AAGGGGGGTT GTTATTATTT TACTGATATG TAAAATATAA TTTGTATAAG AAAATGAGAG
   TTCCCCCCAA CAATAATAAA ATGACTATAC ATTTTATATT AAACATATTC TTTTACTCTC 250        260        270        280        290        300
   GGAGAGGAAA CATGATTCAA AAACGAAAGC GGACAGTTTC GTTCAGACTT GTGCTTATGT
   CCTCTCCTTT GTACTAAGTT TTTGCTTTCG CCTGTCAAAG CAAGTCTGAA CACGAATACA 310        320        330        340        350        360
   GCACGCTGTT ATTTGTCAGT TTGCCGATTA CAAAAACATC AGCCGTAAAT GGCACGCTGA
   CGTGCGACAA TAAACAGTCA AACGGCTAAT GTTTTTGTAG TCGGCATTTA CCGTGCGACT 370        380        390        400        410        420
   TGCAGTATTT TGAATGGTAT ACGCCGAACG ACGGCCAGCA TTGGAAACGA TTGCAGAATG
   ACGTCATAAA ACTTACCATA TGCGGCTTGC TGCCGGTCGT AACCTTTGCT AACGTCTTAC 430        440        450        460        470        480
   ATGCGGAACA TTTATCGGAT ATCGGAATCA CTGCCGTCTG GATTCCTCCC GCATACAAAG
   TACGCCTTGT AAATAGCCTA TAGCCTTAGT GACGGCAGAC CTAAGGAGGG CGTATGTTTC 490        500        510        520        530        540
   GATTGAGCCA ATCCGATAAC GGATACGGAC CTTATGATTT GTATGATTTA GGAGAATTCC
   CTAACTCGGT TAGGCTATTG CCTATGCCTG GAATACTAAA CATACTAAAT CCTCTTAAGG 550        560        570        580        590        600
   AGCAAAAAGG GACGGTCAGA ACGAAATACG GCACAA 3'
   TCGTTTTTCC CTGCCAGTCT TGCTTTATGC CGTGTT 5'
```

RECOMBINANT DNA-MOLECULES AND METHOD FOR PROTEIN PRODUCTION

This application is a continuation, of application Ser. No. 939,244, filed Dec. 5, 1986, and abandoned, which is a continuation of application Ser. No. 336,405, filed Dec. 31, 1981, and abandoned.

BACKGROUND OF THE INVENTION

This invention is concerned with recombinant DNA molecules, and methods for producing proteins by said molecules. The invention is particularly concerned with recombinant DNA molecules that are synthesized in Bacillus strain bacteria and are known to have DNA which codes for exoenzymes excreted by them and that are present in tens of copies in Bacillus strain bacteria; as well as with recombinant DNA molecules modified from the above recombinant DNA molecules that are known to have DNA which contains the regulation and excretion signals of the α-amylase gene of *B. amyloliquefaciens*, to which signals a gene of any protein can be joined. As will be described in the following, these recombinant DNA molecules can be used, for example, to intensify the α-amylase production in Bacillus strain bacteria, and their modifications to produce any protein in Bacillus strain bacteria.

Resent development in molecular biology has created new possibilities for protein production in bacteria by recombinant DNA techniques. In addition to the possibility of producing proteins of eukaryotic cells in bacteria by recombinant DNA techniques, the synthesis of the proteins of the bacteria themselves can be significantly improved by increasing the number of the copies of the desired gene in the cell. The number of the gene copies in a bacterium cell can be increased by joining the gene to such a plasmid or virus DNA molecule as is found in the cell in several, usually 10 to 100, copies. The increased number of the gene copies in a cell usually also leads to a corresponding increase in the protein synthesis expressed by the gene.

Even though several experiments of this type have been carried out using E. coli and plasmid or virus DNA molecules replicating in it as host bacterium, the use of Bacillus strain bacteria as hosts is only beginning (Bryczan et al., Molecular General Genet. 177, 459–467, 1979; Keggins et al., Proc. Natl. Acad. Sci. U.S.A. 75, 1423–1427, 1978; Yoneda et al., Biochem. Biophys. Res. Commun., 91, 1556–1564, 1979). None of the methods publicised so far are concerned with increasing the production of the exoenzyme of a Bacillus strain bacterium in Bacillus strain bacteria in a manner which would allow the gene coding for the exoenzyme to be replicated by joining it to the plasmid that is present in the Bacillus strain bacterium in several copies (Part I of the invention), nor are any of the publicised methods concerned with producing proteins by a method in which the regulation and secretion signals of the gene of the enzyme secreted by the Bacillus strain bacteria have been joined to the gene of the protein desired to be produced (Part II of the invention). As an example of the 1st part of the invention, by which the production of Bacillus strain bacterium exoenzymes can be intensified through increasing the number of the genes of the desired exoenzyme in the cell, the transfer of the Bacillus-α-amylase gene is presented.

DETAILED DESCRIPTION OF THE INVENTION

Figure 1:
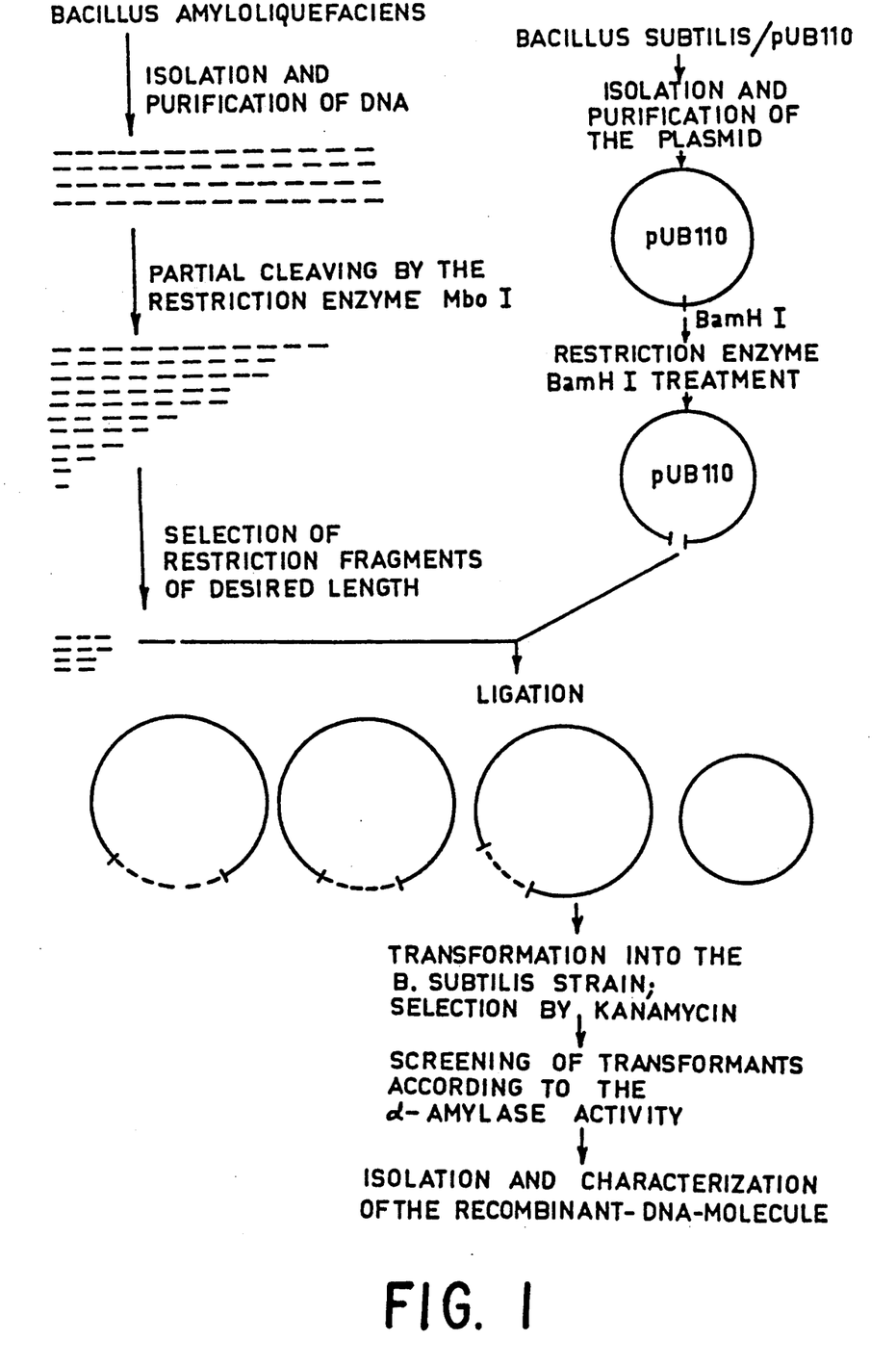
FIG. 1 is a flow sheet illustrating the procedure of one embodiment of the invention in which the recombinant DNA molecule is prepared, isolated and characterized.

FIG. 1 shows the performance of the 1st part of this invention. The genome of the whole bacterium is isolated from the Bacillus strain bacterium producing α-amylase, and cleaved by a restriction enzyme. DNA sequences of a desired length are joined to the plasmid molecule cleaved by the restriction enzyme. According to this invention, the genome of the bacterium can be cleaved by the restriction enzyme MboI, and pUB110 can be used as the plasmid which can be cleaved by the restriction enzyme BamHI. It must be noticed that a corresponding recombinant DNA molecule can be prepared also by using other restriction enzymes or plasmids, and an experienced scientist can choose between various restriction enzyme/plasmid combinations, and still remain within the scope of this invention.

After joining the DNA sequences with the plasmid molecules, the obtained recombinant DNA molecules are transferred into the host bacterium, and from the population of host bacteria those bacterium cells are screened that have received a gene coding for α-amylase, joined to the plasmid. The screening is based on the achieved ability of the transformed cells to produce α-amylase.

Bacillus subtilis strain is used as the host bacterium in this invention. When the above mentioned recombinant DNA molecule has been transferred into the strain, the gene coding for α-amylase is present in it in about 50 copies. This increases the α-amylase production of the strain to about 500 fold, as compared to normal *B. subtilis* strains. The 500-fold increase of the α-amylase production is due, on the one hand, to the regulation signal of the α-amylase gene of the *B. amyloliquefaciens* strain used as the initial strain being about ten times more effective than that of the *B. subtilis* α-amylase gene, and on the other hand, to the number of α-amylase genes growing 50 fold. In laboratory conditions a *B. subtilis* strain containing a recombinant DNA molecule produces 3–5 times more α-amylase than the *B. amyloliquefaciens* strain used in the isolation of the gene.

Figure 2:
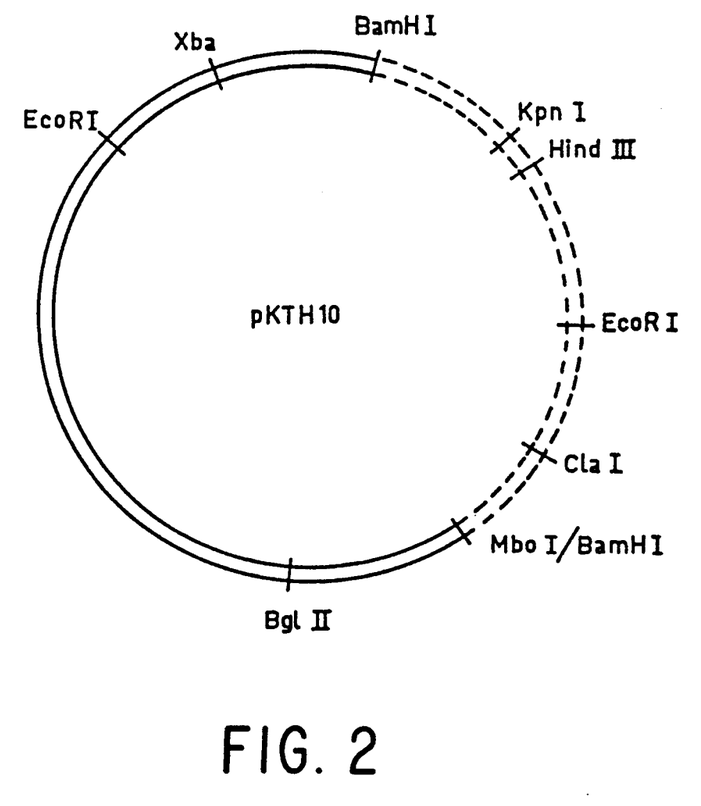
FIG. 2 is a schematic illustration of the plasmid pKTH10 and the general structure of the obtained recombinant DNA molecule.
Figure 3:
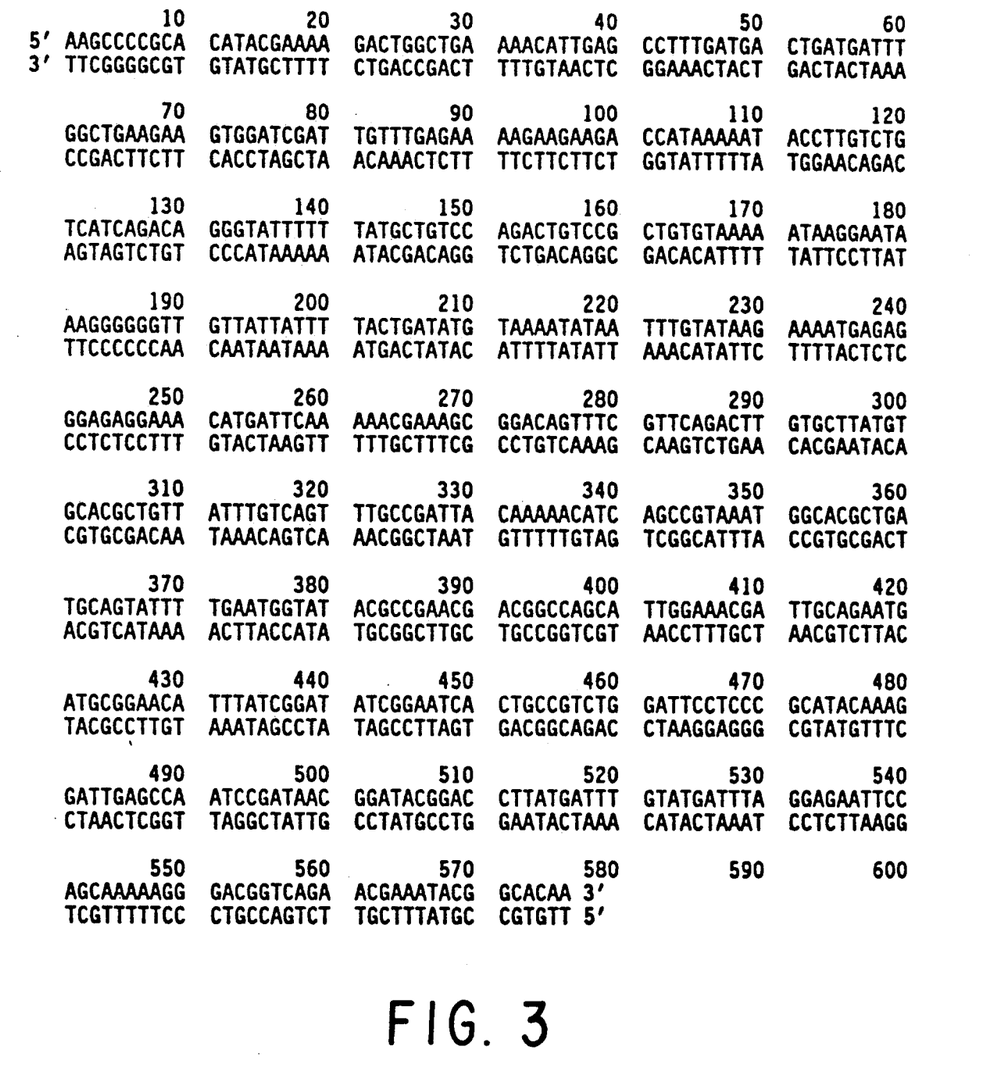
FIG. 3 is a representation of the nucleotide sequence for part of the alpha-amylase gene base.

The recombinant DNA molecule is isolated from the *B. subtilis* strain, and characterized by restriction enzymes and definition of the base order. FIG. 2 shows the pKTH10 of the obtained recombinant DNA molecule, the exclusive restriction enzyme cleavage sites in the α-amylase gene or its regulation signal, and the general structure of the recombinant DNA molecule. FIG. 3 shows part of the α-amylase gene base order starting at the cleavage site of the restriction enzyme EcoRI.

Figure 4:
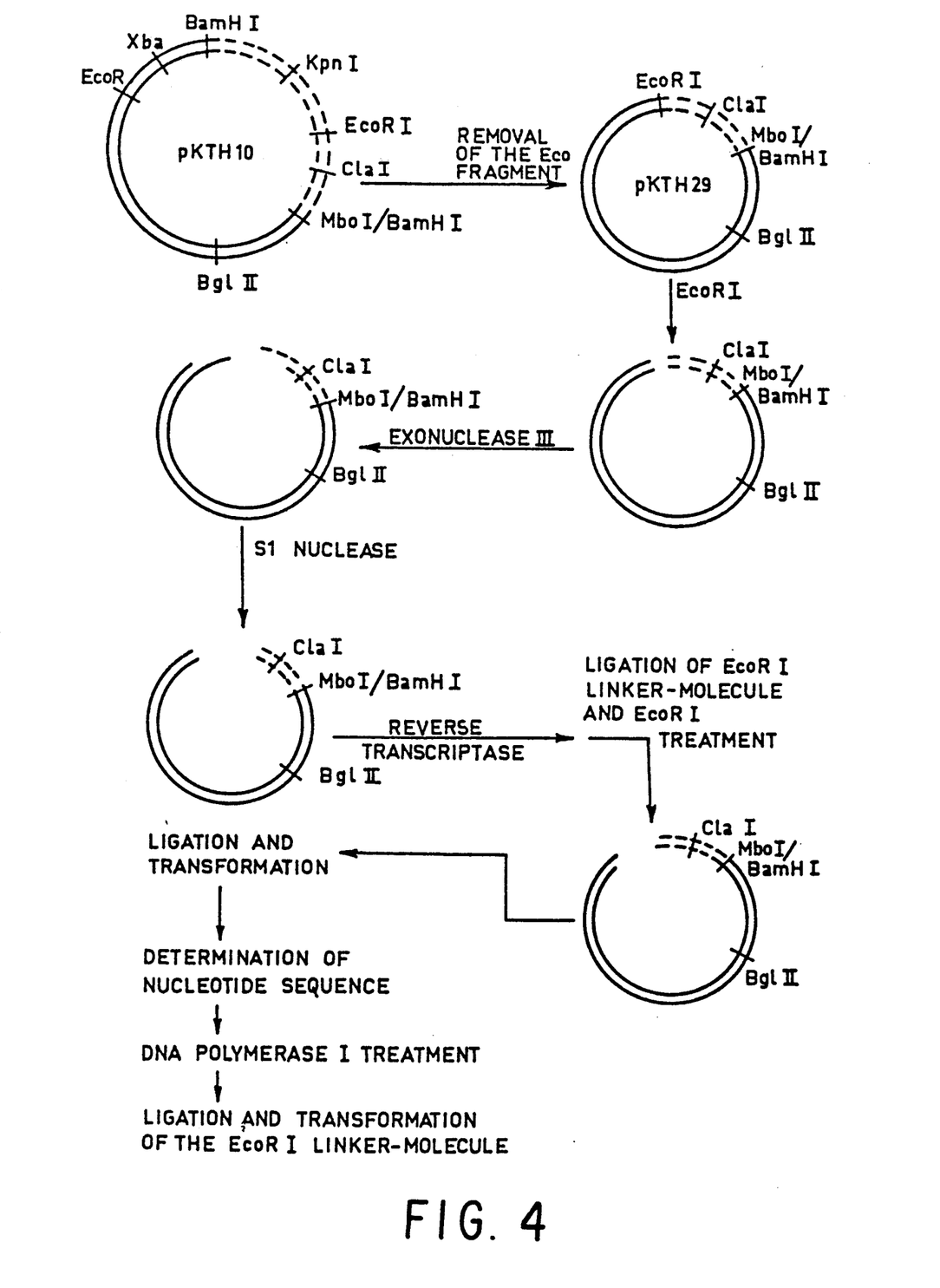
FIG. 4 is a flow sheet illustrating the preparation of the recombinant DNA molecule of the present invention containing the regulation and excretion signals of the Bacillus strain alpha-amylase gene.

The recombinant DNA molecule concerned in this invention consists of the regulation and excretion signals of the Bacillus strain α-amylase gene, and of plasmid molecules that are present in the Bacillus strain bacteria in several copies in such a manner as allows the gene of any protein to be joined at the end of the excretion signal of the α-amylase gene, which results in the desired protein being produced in the Bacillus strain bacterium. The preparation of this recombinant DNA molecule is shown in FIG. 4.

Most of the α-amylase structure gene is first removed by EcoRI restriction enzyme treatment from the recombinant DNA molecule containing the α-amylase gene. The obtained DNA molecule is cleaved by the restriction enzyme and shortened by exonuclease III and S1 nuclease to remove the remaining α-amylase structure gene, whereafter it is secured by a reverse transcriptase enzyme that the ends of the molecule are double-stranded. A DNA linker molecule containing the EcoRI cleavage site is then joined to the cleaved and shortened molecule. The location of the DNA linker in the recombinant DNA molecule is determined by defining the DNA base order at the joining site. The last nucleotides in the α-amylase structure gene are removed by DNA polymerase I treatment, and the new DNA linker is joined at the end of the secretion signal of the α-amylase gene. At this restriction enzyme cleavage site of the DNA linker molecule it is possible to join the structure gene of any other protein, for example, the β-lactamase of E. coli, or the DNA sequence or part of it of any α, β or γ interferon coding for amino acids. The protein coded by the joined gene will then be produced in the Bacillus strain bacterium by the aid of the regulation and excretion signals of the α-amylase gene.

DETAILED DESCRIPTION OF THE PERFORMANCE OF THE 1ST PART OF THE INVENTION

Isolation, purification and cleavage of the genome from Bacillus strain bacteria B. amyloliquefaciens strain was used as the bacterium strain. The strain was grown over night in a rich nutrient solution, the cells were harvested and washed in a 0.0015M sodium citrate-0.015M NaCl buffer. The washed cells were suspended ($2 \times 10^{11}$ cells, i.e. a culture of 200 ml) into 2 ml of 20% w/v saccharose-50 mM Tris-HCl solution (pH 8.0). 20 mg lysozyme, 20 mg pronase and 2 ml 1% w/v Sarkosyl$^R$-0.1M EDTA solution (pH 8.0) were added, and the solution was incubated for 15 hours at 37° C. 6.5 ml H$_2$O and such an amount of solid CsCl as to make the refraction index of the lysate 1.4100, were added, and the lysate was centrifuged (Beckman Ti 50 rotor, 36 000 rpm, 48 hours, 10° C.). The centrifuged lysate was divided into fractions, and those fractions that were presumed to contain the bacterial genome on the basis of their viscosity, were collected and dialysed for 30 hours against a 10 mM Tris-HCl-1 mM EDTA-0.1M NaCl buffer (pH 8.0) at 4° C.).

The obtained genome preparate was extracted three times with phenol, and the phenol was removed by ether extraction. The DNA was purified by centrifugation in linear 15→30% w/v saccharose-0.1M NaCl-50 mM Tris-HCl-1 mM EDTA, 0.1% sodium lauryl sulphate (pH 8.0) gradient; Beckman SW27 rotor, 22 000 rpm, for 16 hours at 22° C., whereafter the gradient was fractioned, and those fractions were collected whose DNA sequences were $\geq 15 \times 10^6$ dalton, and the DNA was precipitated by ethanol.

The genome preparate of B. amyloliquefaciens thus isolated was incompletely cleaved by the restriction enzyme MboI, and the cleaved DNA sequences were sorted out according to their size in the above saccarose gradient (Beckman SW27 rotor, 22 000 rpm, 16 hours at 22° C.). Those fractions whose DNA sequences were $1.5$-$5 \times 10^6$ dalton were harvested and the DNA was precipitated by ethanol.

Isolation and cleavage of the transfer vector by restriction enzyme

The plasmid pUB110 was used as a transfer vector. The plasmid was isolated and purified from the Bacillus subtilis strain SB202 as described earlier (Gryczan et al., J. Bacteriol. 134, 318-329, 1978). The purified plasmid preparate was cleaved with the restriction enzyme BamHI, which has only one cleavage site in the plasmid molecule. The linearity of the plasmid molecule was controlled by gel electrophoresis.

Combination of the B. amyloliquefaciens genome strands to the transfer vector The B. amyloliquefaciens genome strands that had been cleaved by the enzyme MboI and selected on the basis of their size, were mixed with the pUB110 plasmid cleaved by the enzyme BamHI in 10 mM Tris HCl-1 mM EDTA buffer (pH 8.0) in a DNA-concentration ratio of 1:3, with the total volume of 120 μl and with the total DNA concentration of 180 μg/ml. The solution was heated for 5 minutes at 65° C., and 13 μl 66 mM Tris HCl-6.6. mM MgCl$_2$-100 mM dithiothreitol-10 mM ATP buffer (pH 7.8) and 5 μl T$_4$-DNA ligase (20 Weiss units) were added to the chilled solution. The ligase solution was incubated for 3 h at 23° C., and the ligation result was controlled by gel electrophoresis.

Transfer of the recombinant DNA molecule into the host bacterium

A B. subtilis 1A197 strain with the genotype sacA321, metB5, arol1907, amy$^-$, was used as the host bacterium. The strain was obtained from Bacillus Genetic Stock Center (Ohio State University, U.S.A), and its phenotype Amy$^-$ was mapped by bacteriogenetic methods as mutations in the structure gene of the enzyme coding for α-amylase. The strain was made competent, i.e. capable of receiving DNA in a manner described previously (Anagnostopoulos et al., J. Bacteriol. 81, 741-746, 1961). The recombinant DNA molecules prepared by ligation as described above, were mixed with the competent host bacteria, and the mixture was kept for 30 min at 37° C. The mixture was then spread on bacterium plates with kanamycin antibiotics to prevent the growth of all those bacteria that had not received a plasmid. The plates were kept for 30 hours at 37° C., during which time the host bacteria with a plasmid or a B. amyloliquefaciens genome strand joined to it, grew into small colonies.

Detection of host bacteria in which the B. amyloliquefaciens gene coding for α-amylase is joined to plasmid pUB110

The bacterial colonies described above were replicated on new nutrient plates that were grown for 30 hours at 37° C. The obtained bacterial cultures were treated with I-KI solution using a method described earlier (J. Bacteriol. 119, 416-424, 1974), which resulted in a white ring forming round those bacterial colonies that had received a recombinant DNA molecule containing a gene coding for α-amylase. The corresponding colonies were collected from the original bacterium plates and the bacteria were subjected to several successive purification growths.

Isolation and characterization of the recombinant DNA molecule

The recombinant DNA molecule was isolated and purified from the host bacterium by a method described earlier (Cryczan et al., J. Bacteriol. 134, 318–329, 1978). The molecule was characterized by various restriction enzymes, and the location of the gene coding for α-amylase was preliminary determined by following the inactivation of the gene when joining extra DNA sequences at various sites of the recombinant DNA molecule. The base order of the gene coding for α-amylase was then determined by a method described earlier (Maxam, A. and Gilbert, W., Proc. Natl. Acad. Sci. U.S.A. 74, 560–564, 1977).

Determination of the α-amylase activity

The modified host bacterium B. subtilis IHO 6064 (sacA321, metB5), which has a gene coding for α-amylase in plasmid pUB110, was grown in a liquid nutrient medium (Luria broth) by aerating at 37° C. Samples were taken from the culture liquid at 2-hour intervals, from which the α-amylase activity was determined by Phadebas ® tablets.

DETAILED DESCRIPTION OF THE PERFORMANCE OF THE 2ND PART OF THE INVENTION

Removal of EcoRI fragment from plasmid pKTH10

The plasmid pKTH10 was cleaved at the cleavage site EcoRI (FIG. 2). The obtained DNA sequences (about 1 μg) were ligated together again in 66 mM Tris-HCl-6.6 mM $MgCl_2$-100 mM dithiothreitol-10 mM ATP buffer (pH 7.8), and 0.5 μl $T_4$-DNA ligase (2 Weiss units) was added. The ligation solution was incubated for 3 hours at 23° C., whereafter the competent B. subtilis IHO 6064 strain was transformed by it in a manner described above. The cells were spread on bacterium plates containing kanamycin and grown over night at 37° C. An α-amylase-negative colony was screened from the obtained transformants by I-KI method using starch plates, and a plasmid was isolated from the colony in a manner described earlier (Gryczan et al., J. Bacteriol. 134, 318–329, 1978). The missing EcoRI-KpnI-HindIII-EcoRI fragment in the obtained plasmid preparate pKTH29 was controlled by gel electrophoresis.

Shortening of plasmid pKTH29 by exonuclease treatment

The plasmid pKTH29 (100 μl, 500 μg/ml) was cleaved by the restriction enzyme EcoRI. After this treatment, 0.5 μl 1M dithiothreitol and 10 μl exonuclease III (0.25 units, Biolabs) were added to the solution. The solution was incubated for 1–3 minutes at 37° C., and the reaction was stopped in a 70° C. waterbath. The DNA was precipitated from the solution by ethanol and dissolved in a 0.3M NaCl-0.03M sodium-acetate-3 mM $ZnCl_2$ buffer (pH 4.5). 10 μl S1-nuclease (25 units/ml, Boehringer Mannheim) was added and the solution was incubated for 30 minutes at 37° C. and for 10 min at 4° C. After the incubations, the preparate was extracted with phenol, the phenol was removed by ether extraction, and the DNA was precipitated by ethanol. The dried DNA was dissolved into 40 μl 10 mM Tris-HCl-1 mM EDTA buffer (pH 8.0), and 10 μl 150 mM Tris-180 mM KCl-40 mM $MgCl_2$-3.0 dithiothreitol buffer (pH 8.3), 5 μl dNTP mixture, in which to each nucleotide-tri-phosphate 10 mM of the solution was mixed in equimolar ratio, and 2 μl reverse transcriptase enzyme (Beard, 13 units/μl), were added. The solution was incubated for 30 minutes at 37° C. and the reaction was stopped by incubation at 65° C. for 7 minutes. The DNA was purified by preparative agarose electrophoresis (LTG, Low Gelling Temperature), and the plasmid zones that had been dyed with ethidium bromide were cut off from the gel. The DNA was extracted from the agarose by phenol at 65° C., the phenol extraction was repeated at 20° C., and the phenol was removed by ether extraction. The DNA was precipitated by ethanol, the precipitate was washed with 70% ethanol and dried.

Phosphorylation of EcoRI linker molecule and its combination to the plasmid

5 μl $^{32}$Py ATP (10 mCi/ml, 3000 Ci/mol), 1.7 μl 600 mM Tris-HCl-66 mM $MgCl_2$-100 mM dithiothreitol buffer (pH 8.0) and 0.5 μl $T_4$-polynucleotidekinase were added to 10 μl EcoRI linker molecule solution (EcoRI linker, Collaborative Research, 50 μg/ml). The solution was incubated for 30 minutes at 37° C., whereafter 5 μl 10 mM ATP was added, and the incubation was continued for 30 min at 37° C. The dried pKTH29 preparate that had been treated with exonuclease, was dissolved into 5 μl of the solution containing phosphorylated EcoRI-linker-molecule described above. 0.5 μl 10 mM ATP, 0.5 μl 1 mM spermidine and 0.5 μl $T_4$-DNA-ligase (2 Weiss units) were added to the solution. The solution was incubated for 3 hours at 23° C., whereafter it was diluted to 20 μl in 40 mM Tris-HCl-100 mM NaCl-10 mM $MgCl_2$-buffer (pH 7.6). 15 units of EcoRI enzyme (Biolabs) were added, and the solution was incubated for 12 h at 37° C. The reaction was stopped by incubation at 65° C. for 10 minutes. The preparate treated with EcoRI was gelfiltered through 1 ml Sepharose 4B column. 2 mM Tris-HCl-0.1 mM EDTA (pH 7.5) was used as elution buffer in the filtering. The filtrate was harvested in 35 μl fractions, and the fractions containing plasmid were identified by their radioactivity, collected and dried. The dried DNA was dissolved into 20 μl 66 mM Tris-HCl-6.6 mM $MgCl_2$-10 mM dithiothreitol buffer (pH 8.0), and 1.5 μl 10 mM ATP and 0.3 μl $T_4$-DNA-ligase were added. the solution was incubated for 3 hours at 23° C., whereafter the competent B. subtilis IHO 6064 strain was transformed by the plasmid preparate, and the cells were cultivated on bacterium plates containing kanamycin.

The plasmids were isolated from the transformants by a method described earlier (Gryczan et al., J. Bacteriol. 134, 318–329, 1978), and the plasmids were first characterized by gel electrophoresis, whereafter their DNA base sequence at both ends of the EcoRI linker molecule was determined. In this way, the plasmid pKTH 38 was obtained from the plasmid pKTK 29. In the plasmid pKTH 38, the EcoRI linker molecule is located 90 nucleotide pairs after the cleavage site of the excretion signal in the area of the α-amylase structure gene. In order to join the linker molecule at the joining site of the excretion signal or in the immediate vicinity thereof, the plasmid pKTH 38 was cleaved with EcoRI. Three portions of 10 μg of the cleaved plasmid were each suspended in 115 μl 20 mM Tris, 600 mM NaCl, 12 mM MgCl$_2$, 12 mM CuCl$_2$, 1 mM EDTA buffer (pH 8.1). 10 μl BAL-31 enzyme (Bethesda Research Laboratories, BRL, 40 U/ml) was added to each plasmide portion, and the tubes were incubated for 5, 6 and 7 minutes in a water bath of 30° C. The reaction was stopped by adding 0.5M EDTA, pH 8.0, so as to obtain a final concentration of 12 mM. The DNA portions treated with BAL-31 were combined, extracted twice with phenol and precipitated with ethanol. The ethanol precipitate was suspended in 75 μl 63 mM Tris, 6.3 mM MgCl$_2$ buffer (pH 8.0), and to the solution were added 5 μl 1 mM dATP, 1 mM dGTP, 1 mM dCTP, and 1 mM dTTP, and finally 5 μl T4 polymerase (PL-Biochemicals, 5 U/μl). The solution was incubated for 80 minutes at 11° C. The reaction was stopped by adding 0.5 EDTA as above, and the solution was extracted with phenol and the DNA was precipitated with ethanol. The ethanol precipitate was dissolved in 250 μl 10 mM Tris, 1 mM EDTA buffer (pH 8.0). To 55 μl of this solution were added 50 μl phosphorylated Hind III linker molecule (BRL, 75 pmol), 5 μl 660 mM Tris, 100 mM MgCl$_2$, 50 mM dithiothreitol buffer (pH 7.5), and 10 μl T4 DNA ligase (BRL, 2 U/μl). The mixture was incubated for 15 hours at 15° C. and for 10 minutes at 65° C. The DNA was precipitated by adding isopropanol, the DNA precipitate was washed with 70% ethanol and, after drying in vacuo, suspended in 100 μl 10 mM Tris, 50 mM NaCl, 5 mM MgCl, 5 mM dithiothreitol buffer (pH 8.0). 3 μl of Hind III restriction enzyme (BRL, 10 U/μl) was added to the suspension, and the solution was incubated for 4 hours at 37° C. and for 10 minutes at 65° C., the DNA was purified by electrophoresis, 0.8% LGT agarose gel (Marine Colloids Inc.), 30 V, 15 hours. The linear plasmid zone was cut off from the gel, the DNA was extracted at 65° C. with phenol and was precipitated with ethanol. The ethanol precipitate was dissolved in 35 μl 66 mM Tris, 10 mM MgCl, 5 mM dithiothreitol buffer (pH 7.5) to which was added 1.5 μl 10 mM rATP and 1.5 μl T4 DNA ligase (BRL, 2 U/μl). The mixture was incubated for 3 hours at 22° C. and transformed into the competent B. subtilis IHO 6135 strain, and the cells were cultivated on nutrient medium plates containing kanamycin. The plasmids were isolated from the transformants according to a method described earlier, and the location of the Hind III linker molecule in the plasmids was determined by means of DNA sequencing. In this way a series of plasmids was obtained in which the Hind III linker molecule is located immediately after the excretion signal or in different positions after the cleavage site of the excretion signal in the area of the α-amylase structure gene.

|  | -31 Met ATG | Phe ATT | Gln CAA | -3 Thr ACA | Ser TCA | -1 Ala GCC | +1 Val GTA | Asn AAT | Gly GGC | Thr ACG | Leu CTG | Met ATG | Gln CAG | Tyr TAT | Phe TTT | Glu GAA | Trp TGG | Tyr TAT | Thr ACG | Pro CCG | Asn AAC |
|---|---|---|---|---|---|---|---|---|---|---|---|---|---|---|---|---|---|---|---|---|---|
| pKTH 10 | ATG | ATT | CAA ... | ACA | TCA | GCC | GTA | AAT | GGC | ACG | CTG | ATG | CAG | TAT | TTT | GAA | TGG | TAT | ACG | CCG | AAC |
| pKTH 50 | ATG | ATT | CAA ... | ACA | TCA | GCC | GCAAGCTTGC | | | | | | | | | | | | | | |
| pKTH 51 | ATG | ATT | CAA ... | ACA | TCA | GCC | GCAAGCTTGC | | | | | | | | | | | | | | |
| pKTH 52 | ATG | ATT | CAA ... | ACA | TCA | GCC | G GCAAGCTTGC | | | | | | | | | | | | | | |
| pKTH 53 | ATG | ATT | CAA ... | ACA | TCA | GCC | GTA | AAT | GGC | AC GCAAGCTTGC | | | | | | | | | | | |
| pKTH 54 | ATG | ATT | CAA ... | ACA | TCA | GCC | GTA | AAT | GGC | ACG | GCAAGCTTGC | | | | | | | | | | |
| pKTH 55 | ATG | ATT | CAA ... | ACA | TCA | GCC | GTA | AAT | GGC | ACG | C GCAAGCTTGC | | | | | | | | | | |
| pKTH 56 | ATG | ATT | CAA ... | ACA | TCA | GCC | GTA | AAT | GGC | ACG | CT GCAAGCTTGC | | | | | | | | | | |
| pKTH 57 | ATG | ATT | CAA ... | ACA | TCA | GCC | GTA | AAT | GGC | ACG | CTG | ATG | CAG | TAT | TTT | G GCAAGCTTGC | | | | | |
| pKTH 58 | ATG | ATT | CAA ... | ACA | TCA | GCC | GTA | AAT | GGC | ACG | CTG | ATG | CAG | TAT | TTT | GAA | TGG | GCAAGCTTGC | | | |
| pKTH 59 | ATG | ATT | CAA ... | ACA | TCA | GCC | GTA | AAT | GGC | ACG | CTG | ATG | CAG | TAT | TTT | GAA | TGG | TAT | ACG | CCG | GCA ... |

The DNA sequence coding for the amino acids of any desired protein can be joined to the cleavage sites formed by these Hind III linker molecules whereby, as appears from the above examples, a bacterium of the Bacillus strain will produce and excrete said protein on its substrate.

A wide variety of proteins may be produced as illustrated by the following listing, presented by general categories:

A. Antigenic proteins of microbes and protozoa

Capsule, outer membrane and Fimbria proteins from the following sources: *Bacteroides fragilis*, Fusobacterium spp., *Bordetella pertussis, Haemophilus influenzae, Yersinia entercolitica, Yersinia pestis, Branhamella catarrhalis, Escherichia coli, Klebsiella pneumonia, Vibrio cholerae, Proteus mirabilis, Pseudomonas aeruginosa, Serratia marcescens, Legionella pneumophila, Neisseria gonorrhoeae, Neisseria meningitidis, Salmonella typhimurium, Salmonella typhi, Salmonella paratyphi B, Mycobacterium tyberculosis, Chlamydia trachomatis*, and Shigella spp.

Protein toxins produced by the following bacteria: *Staphylococcus aureus, Pseudomonas aeruginosa*, Clostridium spp., *Escherichia coli, Yersinia pestis, Vibrio cholerae, Bordetella pertussis*, M-protein of the *Streptococcus pyogenes* bacterium, Excreted enzymes of *Streptococcus mutans.*

Surface proteins of the following organisms (in all phases of development): Plasmodium spp., Toxoplasma spp., Leishmania spp., Schistosoma spp., Trypanosoma spp.

Membrane proteins of the following microorganisms: *Mycoplasma pneumoniae, mycoplasma hominis*, Contagious protein of Streptococcus spp., and Contagious protein of *Staphylococcus aureus.*

B. Antigen proteins or viruses

HA and NA proteins of myxoviruses (influenza A H1-H12, influenza B, influenza C); HN and F proteins of paramyxoviruses (parainfluenze 1-4, Newcastle disease virus, Measles virus, Respiratory syncytial virus, Parotitis virus, Distemper virus); G protein of Rabies virus; E1 and E2 proteins of alfaviruses (Chikungunya, Western, Easter, Venezuelan equine encephalitis virus, O'nyong-nyong virus, Semliki Forest virus, Sindbis virus); V1 and V3 proteins of flavin viruses (Denque 1-4, Japanese encephalitis virus, Mite encephalitis viruses, Murray Valley encephalitis virus, Kyasanur Forest disease virus, Looping ill virus, Omsk hemorrhagic fever virus); surface proteins of German measles virus; surface proteins of Hog Cholera virus; surface proteins of Equine arthritisvirus; G1 and G2 proteins of Bunya viruses (Rift Valley fever virus, Crimean hemorrhagic fever virus, California encephalitis virus, Phlebotomus fever virus); G1 and G2 proteins of arena viruses (Lassa fever virus, Lymphocytic chorion meningitis virus); proteins V1-V4 of picorna viruses (polio 1-3, Coxsackie A viruses 1-24, Coxsackie B viruses 1-6, ECHO viruses 1-8, 11-34, hepatitis A virus, Human rhino viruses 1-113); surface proteins of rota viruses; surface proteins of herpes viruses (HSV 1, 2, Cytomegalo virus, Epstein-Barr virus, Equine abortion virus); VP1-VP3 proteins of papova viruses (BK virus, Human wart virus); proteins of parvo viruses (mink enteritis virus, Bovine parvo virus, Feline parvo virus, Procine parvo virus); structure proteins of Human hepatitis B virus; surface proteins of Ebola and Marburg viruses; and Hexone, pentone and fiber proteins of adeno viruses, (Human adeno viruses 1-33).

C. Industrial enzymes alpha-amylase: (*B. subtilis*, malt, *A. oryzae*)
Amino acid acylase: (Bacillus spp.)
Amyloglucosidase: (*A. niger*, Rhizopus sp.)
Bromelain: (Ananas)
Phisine: (Fig)
beta-galactosidase: (*A. niger*)
beta-gulcanase: (*B. subtilis*, Aspergillus sp.)
Glucose-isomerase: (*L.brevis, P.notanum*, streptomyces sp.)
Glucoseoxidase (*A. niger*)
Hemicellulase (*A. niger, Trichoderma reesei*, Bascillus spp.)
Invertase (*S. cerevisiae*)
Catalase: (*A. niger*)
Collagenase: (*Clostridium histolyticum*)
Xsylanase: (*A. niger, trichoderma reesei*, Bacillus spp.)
Lactase: (*S. fragilis, S. lactis, E. coli*, Aspergillus sp.)
Lipase: (Mould, Yeast)
Naringinase: (*A. niger*)
Pancreatin: (Pancreas)
Papain: (Papaya)
Pectinase: (*A. niger*, Penicillium sp.)
Penicillinamidase: (Bacillus spp.)
Penicillinase: (Bacillus spp.)
Pepsin: (Animal abdomen)
Protease: (*A. oryzae, B. subtilis*)
Pullulanase: (*Aerobacter aerogenes*)
Isoamylase: (*Escherichia intermedia*, Pseudomonas sp.)
Rennin (Calf stomach, *M. miehei, Endothia parasitica*)
Ribonuclease: (*B. subtilis*, Mould, *A. niger*)
Cellulase: (*A. niger, Trichoderma reesie*)
Streptokinase: (*Streptococcus hemolyticus*)
Trypsin: (Pancreas)

EXAMPLE 1

Production of the β-lactamase enzyme of *E. coli* from the *Bacillus substitus* strain The plasmid pKTH was opened by the Hind III enzyme, and to the cleavage site was joined a gene coding for β-lactamase of *E. coli* from which the promotor and excretion signal areas had been removed. The hybrid plasmid obtained was transformed into the competent *B. subtilis* IHO 6140 strain by selecting the cells that had received the plasmid, on the basis of the kanamycin resistance, and the cells were cultivated on nutrient medium plates containing kanamycin. The transformants were screened with respect to the yield by suspending each colony in 100 μl 0.1 mM nitrosephin, 0.1M K-phosphate solution (pH 7.0). Liquid cultures were made of the colonies which gave a positive result in the nitrosephin test (the colour of the solution changed into red) for determination of the activity of the β-lactamase enzyme produced. The IHO 6140-B. subtilis strain which had been transformed by the plasmid pKTH 50 was used as control. The strains were grown in a SMS solution (Spizizen minimal salts) to which had been added 0.5% glycerol, 1% soluble starch, and 5 μg/ml kanamycin. The cultures were grown at 37° C. while shaking. About 5 hours after a logarithmic growth period ($Klett_{67}\sim250$), the cultures were centrifuged 10.000 g 5 minutes and the supernatant was recovered. The cells were suspended in 0.1M potassium phosphate buffer (pH 7.0) to their original growing volume. The β-lactamase activity was determined in the cell and supernatant fractions by following spectrophotometrically the disintegration of cephalotin. The following results were obtained from the determination.

|  | β-lactamase activity (U/ml)* | |
|---|---|---|
|  | cells | supernatant |
| B. subtilis IHO 6140/pKTH 50 β-lactamase | 60 | 3000 |
| B. subtilis IHO 6140/pKTH 50 | <10 | <10 |

*1 U of β-lactamase disintegrates 1 μmol penicillin G in 1 minute at 37° C.

EXAMPLE 2
Production of leukocyte interferon in the *Bacillus subtilis* strain The plasmid pKTH 53 was cleaved by the Hind III enzyme, and to the cleavage site was joined the DNA sequence coding for the leukocyte interferon (α-2) from which the part coding for the excretion signal had been removed. The obtained hybrid plasmid was transformed into the competent IHO 6140 *B. subtilis* strain by selecting the cells that had obtained the plasmid, on the basis of the kanamycin resistance. The transformants were screened by a colony hybridization method (Grünstein, M. and Hogness, D.S., Proc. Natl. Acad. Sci. (U.S.) 72, 3961–3965, 1975) while using as probe the DNA coding for the interferon, marked $^{125}$J. The bacterium colonies containing interferon-DNA were grown in Luria broth to which had been added 2% soluble starch and 5 μg/ml kanamycin, while shaking at 37° C. The culture was centrifuged 4 hours after the logarithmic growth period (Klett$_{67}$~300) 10.000 g, 5 min. The supernatant was recovered, and the cells were suspended to their original growing colume in a 0.9% NaCl solution. The interferon activity was determined in the cell and supernatant fractions. The *B. subtilis* IHO 6140-pKTH 53 strain was used as control in the determinations. The following results were obtained from the determinations:

|  | Interferon activity (I.U./ml) | |
|---|---|---|
|  | cells | supernatant |
| B. subtilis IHO 6140/ pKTH 53-IF | 3000 | 200 000 |
| B. subtilis IHO 6140/ pKTH 53 | <20 | <20 |

What I claim is:

1. A recombinant DNA molecule comprising a plasmid which is capable of multiplying in Bacillus strain bacteria, the regulation and secretion signal sequences of the α-amylase gene of *B. amyloliquefaciens*, and the DNA sequence encoding the amino acids of a desired protein or polypeptide, said DNA sequence being downstream of said secretion signal sequence, with the proviso that said desired protein is not α-amylase of *B. amyloliquefaciens*.

2. A recombinant DNA molecule as claimed in claim 1 in which said DNA sequence encoding the amino acids of the desired protein codes for an interferon selected from the group consisting of α-interferon and β-interferon.

3. A recombinant DNA molecule as claimed in claim 1 in which said DNA sequence codes for β-lactamase of *E. coli*.

4. A recombinant DNA molecule as claimed in claim 1 in which the plasmid contained in said DNA molecule is pUB110.

5. A recombinant DNA molecule according to claim 1 wherein said regulation and secretion signal sequences of the α-amylase gene has the following nucleotide sequence:

```
              10         20         30
5'AAGCCCCGCA CATACGAAAA GACTGGCTGA
3'TTCGGGGCGT GTATGCTTTT CTGACCGACT 40         50         60
  AAACATTGAG CCTTTGATGA CTGATGATTT
  TTTGTAACTC GGAAACTACT GACTACTAAA 70         80         90
  GGCTGAAGAA GTGGATCGAT TGTTTGAGAA
  CCGACTTCTT CACCTAGCTA ACAAACTCTT 100        110        120
  AAGAAGAAGA CCATAAAAAT ACCTTGTCTG
  TTCTTCTTCT GGTATTTTTA TGGAACAGAC 130        140        150
  TCATCAGACA GGGTATTTTT TATGCTGTCC
  AGTAGTCTGT CCCATAAAAA ATACGACAGG 160        170        180
  AGACTGTCCG CTGTGTAAAA ATAAGGAATA
  TCTGACAGGC GACACATTTT TATTCCTTAT 190        200        210
  AAGGGGGGTT GTTATTATTT TACTGATATG
  TTCCCCCCAA CAATAATAAA ATGACTATAC 220        230        240
  TAAAATATAA TTTGTATAAG AAAATGAGAG
  ATTTTATATT AAACATATTC TTTTACTCTC 250        260        270
  GGAGAGGAAA CATGATTCAA AAACGAAAGC
  CCTCTCCTTT GTACTAAGTT TTTGCTTTCG 280        290        300
  GGACAGTTTC GTTCAGACTT GTGCTTATGT
  CCTGTCAAAG CAAGTCTGAA CACGAATACA 310        320        330
  GCACGCTGTT ATTTGTCAGT TTGCCGATTA
  CGTGCGACAA TAAACAGTCA AACGGCTAAT

340
  CAAAACATC AGCC
  GTTTTTGTAG TCGG
```

6. A recombinant DNA molecule as claimed in claim 1 in which the DNA sequence coding for said desired protein or polypeptide is joined to a DNA sequence selected from the group consisting of

```
5' CTG TTA TTT GTC AGT TTG CCG ATT ACA AAA ACA TCA GCC,
5' CTG TTA TTT GTC AGT TTG CCG ATT ACA AAA ACA TCA GCC G,
5' CTG TTA TTT GTC AGT TTG CCG ATT ACA AAA ACA TCA GCC GT,
5' CTG TTA TTT GTC AGT TTG CCG ATT ACA AAA ACA TCA GCC GTA,
5' CTG TTA TTT GTC AGT TTG CCG ATT ACA AAA ACA TCA GCC GTA A, and
5' CTG TTA TTT GTC AGT TTG CCG ATT ACA AAA ACA TCA GCC GTA AA.
```

* * * * *

UNITED STATES PATENT AND TRADEMARK OFFICE
CERTIFICATE OF CORRECTION

PATENT NO. : 5,010,015
DATED : April 23, 1991
INVENTOR(S) : Ilkka Palva

It is certified that error appears in the above-indentified patent and that said Letters Patent is hereby corrected as shown below:

Title page, item [30], Foreign Application Priority Data, delete "[FR] France" and replace therein -- [FI] Finland --.

Signed and Sealed this

Seventh Day of March, 1995

*Attest:*

BRUCE LEHMAN

*Attesting Officer*        *Commissioner of Patents and Trademarks*